United States Patent [19]

Yabe et al.

[11] Patent Number: 5,575,753

[45] Date of Patent: *Nov. 19, 1996

[54] ENDOSCOPIC APPARATUS USING A COVERED TYPE ENDOSCOPE FITTED IN AN ENDOSCOPE COVER

[75] Inventors: Hisao Yabe, Hachioji; Yoshihiro Iida, Tama; Akira Suzuki; Hideo Itoh, both of Hachioji; Yoshio Tashiro, Hino; Minoru Yamazaki; Osamu Tamada, both of Hachioji, all of Japan

[73] Assignee: Olympus Optical Co., Ltd., Tokyo, Japan

[*] Notice: The term of this patent shall not extend beyond the expiration date of Pat. No. 5,419,311.

[21] Appl. No.: 38,620

[22] Filed: Mar. 25, 1993

[30] Foreign Application Priority Data

| Mar. 5, 1993 | [JP] | Japan | 5-009176 U |
| Mar. 5, 1993 | [JP] | Japan | 5-009177 U |
| Mar. 5, 1993 | [JP] | Japan | 5-045564 |

[51] Int. Cl.$^6$ .................................................. A61B 1/04
[52] U.S. Cl. .......................................... 600/123; 600/121
[58] Field of Search .......................... 128/4, 6; 600/121, 600/122, 123, 124, 125, 132, 131

[56] References Cited

U.S. PATENT DOCUMENTS

| Re. 34,110 | 9/1992 | Opie . | |
| 3,162,190 | 12/1964 | Del Gizzo . | |
| 4,646,722 | 3/1987 | Silverstein | 128/4 |
| 4,721,097 | 1/1988 | D'Amelio | 128/4 |
| 4,741,326 | 5/1988 | Sidall | 128/4 |
| 4,825,850 | 5/1989 | Opie | 128/4 |
| 4,869,238 | 9/1989 | Opie | 128/6 |
| 4,886,049 | 12/1989 | Darras | 128/4 |
| 4,907,395 | 3/1990 | Opie | 53/434 |
| 4,991,564 | 2/1991 | Takahashi | 128/4 |
| 4,991,565 | 2/1991 | Takahashi | 128/4 |
| 4,997,084 | 3/1991 | Opie | 206/364 |
| 5,050,585 | 9/1991 | Takahashi | 128/4 |
| 5,058,567 | 10/1991 | Takahashi | 128/4 |
| 5,201,908 | 4/1993 | Jones | 128/4 |
| 5,329,935 | 7/1994 | Takahashi | 128/4 |
| 5,419,311 | 5/1995 | Yabe et al. | 600/124 |
| 5,458,132 | 10/1995 | Yabe et al. | 600/121 |
| 5,460,167 | 10/1995 | Yabe et al. | 600/123 X |

FOREIGN PATENT DOCUMENTS

| 0184778 | 6/1986 | European Pat. Off. . |
| 0310515 | 4/1989 | European Pat. Off. . |
| 0338567 | 10/1989 | European Pat. Off. . |
| 0341719 | 11/1989 | European Pat. Off. . |
| 0341718 | 11/1989 | European Pat. Off. . |
| 0349479 | 1/1990 | European Pat. Off. . |
| 0440252 | 8/1991 | European Pat. Off. . |

(List continued on next page.)

*Primary Examiner*—Richard J. Apley
*Assistant Examiner*—Beverly M. Flanagan
*Attorney, Agent, or Firm*—Armstrong, Westerman, Hattori, McLeland & Naughton

[57] ABSTRACT

An covered endoscope type of endoscopic apparatus has a covered endoscope and a cover for covering the covered endoscope. The covered endoscope has an elongated flexible inserted portion, an operated portion formed on the base end side of the inserted portion, and a universal cord extending from a side portion of the operated portion. The cover is formed of an inserted portion cover member, an operated portion cover member and a cord cover which cover the inserted portion, the operated portion and the universal cord of the covered endoscope, respectively. An operated endoscope portion fixation mouth member having a forceps inlet and an expansion tube mouth to which an expansion tube provided on an expander is connected is provided at a base end of the inserted portion cover member. An air supply tube, a water supply tube and an aspiration tube are inserted through the inserted portion cover member, the operated portion cover member and the cord cover. The overall length of the aspiration tube, the air supply tube and the water supply tube of the cover is set so as to be greater than the sum of the lengths of the inserted portion, operated portion and universal cord of the covered endoscope.

7 Claims, 18 Drawing Sheets

FOREIGN PATENT DOCUMENTS

| | | |
|---|---|---|
| 0440254 | 8/1991 | European Pat. Off. . |
| 0444429 | 9/1991 | European Pat. Off. . |
| 3909290 | 10/1989 | Germany . |
| 51-47587 | 4/1976 | Japan . |
| 51-103891 | 8/1976 | Japan . |
| 52-95284 | 7/1977 | Japan . |
| 58-44033 | 3/1983 | Japan . |
| 62-177701 | 11/1987 | Japan . |
| 1-140902 | 9/1989 | Japan . |
| 2-57228 | 2/1990 | Japan . |
| 2-54734 | 11/1990 | Japan . |
| 3-13105 | 2/1991 | Japan . |
| 3-37029 | 2/1991 | Japan . |
| 3-37030 | 2/1991 | Japan . |
| 3-29634 | 2/1991 | Japan . |
| 3-29635 | 2/1991 | Japan . |
| 3-221024 | 9/1991 | Japan . |
| 3-101906 | 10/1991 | Japan . |
| 3-101907 | 10/1991 | Japan . |
| 3-101905 | 10/1991 | Japan . |
| 3-101904 | 10/1991 | Japan . |
| 3-101903 | 10/1991 | Japan . |
| 3-101902 | 10/1991 | Japan . |
| 3-101901 | 10/1991 | Japan . |
| 4-325138 | 11/1992 | Japan . |

⇧ UP

⇧ UP

ENDOSCOPIC APPARATUS USING A COVERED TYPE ENDOSCOPE FITTED IN AN ENDOSCOPE COVER

BACKGROUND OF THE INVENTION

1. Field of the Invention

This invention relates to an endoscopic apparatus using a covered type endoscope which is fitted in an endoscope cover by expanding the cover with an endoscope cover expander.

2. Description of the Related Art

Recently, uses of endoscopes have been increased in the field of medical treatment. During use of an endoscope in the field of medical treatment, it is possible that when the endoscope is inserted into a living body, body fluids will attach to an observation window provided in a fore end portion of an inserted section of the endoscope so that objects cannot be suitably observed through the window. To avoid this problem, an air supply tube and a water supply tube are provided to remove body fluids or the like attached to the observation window by blowing a fluid against the observation window by an operation at the operator side of the apparatus. In some cases, an aspiration tube for discharging unnecessary body fluids in an aspiration manner is provided.

There are endoscopes having a forceps channel (treatment instrument channel) which makes it possible to sample a tissue with biopsy forceps or to perform a treatment with a certain treatment instrument.

In the case of an endoscope provided with tubes and/or a forceps channel such as those mentioned above, washing and sterilizing operations are performed after use of the endoscope in a patient's body. However, the time required to achieve the desired effect of washing and sterilization is so long that the efficiency of use of the endoscope is considerably low, and sterilizing operations are troublesome.

In view of this problem, a covered type endoscope has been proposed which is used while being covered with an endoscope cover so that it can be maintained in a clean state during use, and which therefore require no washing and sterilizing operations.

For example, Japanese Patent Laid Open No. 3-29634 discloses a cover (sheath) for covering an inserted portion of an endoscope by being fitted around the inserted endoscope portion. To facilitate the operation of setting the inserted endoscope portion in the cover and the operation of detaching the endoscope portion from the cover, a cover portion for covering the inserted endoscope portion when the inserted endoscope portion is inserted into the cover is constructed so as to be able to expand by being supplied with air from a cover expander.

Fluid tubes are provided in the cover of the conventional covered type endoscope described above. During endoscopic examination, the fluid tubes of the cover and a universal cord of the covered type endoscope connect the endoscope in the cover and an external unit cart on which external units, such as a light source, air-supply and water-supply units, are mounted. The fluid tubes of the endoscope cover are connected to a fluid controller, and air and water are supplied and aspirated through the tubes through end portions formed at a fore end of the cover.

During examination handling of the endoscope, operations of twisting an operated endoscope portion connected to the inserted endoscope portion and inserting or extracting the operated portion are frequently performed. During such operations, a considerably large tensile force is applied to the fluid tubes of the endoscope cover and the universal cord of the covered endoscope. If the tensile force is larger than an allowable level, the fluid tubes of the endoscope cover or the universal cord of the covered endoscope is detached from the external unit. If the universal cord of the endoscope is detached, it may be reconnected. However, if the fluid tubes of the endoscope cover are detached, there is a risk of the fluid tubes and the external unit being contaminated. Thus, the conventional covered type endoscope has a drawback in terms of safety from infection.

To use the above-described conventional covered type endoscope for examination, an operation of attaching the covered type endoscope and the endoscope cover must be initially. It is necessary to perform this operation with the greatest of care so that the sterilized endoscope cover is not contaminated by being brought into contact with a floor and other things.

However, the endoscope cover is formed of an outer covering for the inserted portion of the covered endoscope and fluid tubes extending from the outer covering and is so long that it is difficult for an operator to perform the attachment operation by keeping the eyes upon the whole of the endoscope cover so that the sterilized endoscope cover is not contaminated, and there is a strong possibility of the endoscope cover being contaminated.

An aspiration tube may be used as a treatment instrument insertion path. Also, in the case of an operation of simultaneously using a plurality of treatment instruments, a covered type endoscope having a plurality of treatment instrument insertion paths and a plurality of aspiration tubes is used.

At the time of aspiration with a covered type endoscope having a plurality of treatment instrument insertion paths and a plurality of aspiration tubes, it is necessary to select the aspiration tubes according to examination situations. That is, the operator determines and sets the amount of aspiration according to various situations, including a situation where a large amount of a foul matter is to be aspirated, a situation where profuse bleeding is caused, a situation where it is desirable to perform soft aspiration without giving an impetus upon a mucous membrane, and a situation where a treatment instrument is inserted or not inserted in each aspiration tube.

However, an aspiration control valve of conventional endoscopic apparatuses using a disposable endoscope cover is provided in an external control unit, and the operator must operate it by reaching his or her hand to the external unit or operate it in a remote control manner with an expensive controller. In either case, a troublesome operation is required.

SUMMARY OF THE INVENTION

An object of the present invention is to provide a covered type endoscope free from the risk of detachment of fluid tubes of an endoscope cover, and capable of safe examination.

Another object of the present invention is to provide a covered type endoscope to which an endoscope cover can be easily fitted while maintaining a sterilized state.

Still another object of the present invention is to provide a covered type endoscope having a simple construction, low-priced, and having improved operability such that an operator can easily change aspiration tubes.

To achieve these objects, according to the present invention, there is provided a covered endoscope type endoscopic apparatus comprising an endoscope having an inserted portion inserted into a body cavity to obtain an observed image and transmission means for transmitting the observed image, an endoscope cover capable of being fitted around the endoscope and having a fore end component portion, a base end component portion and a soft tubular portion, and at least one fluid passage having at least a portion provided in the tubular portion. The overall length of the fluid passage is longer than the overall length of the endoscope including the inserted portion and the transmission means.

These and other features and advantages of the present invention will become apparent from the following detailed description of preferred embodiments of the invention.

BRIEF DESCRIPTION OF THE DRAWINGS

FIGS. 1 to 6 relate to a first embodiment of the present invention;

FIG. 1 is an illustration showing the overall construction of a covered type endoscopic apparatus having a covered type endoscope;

FIG. 3 is a cross-sectional view of the inserted portion cover member;

FIG. 4 is an illustration showing a state of connection between an air supply tube and a water supply tube of the inserted portion cover;

FIG. 6 is an illustration showing an example of the state of connection between a universal cable, the air supply tube, the water supply tube and the aspiration tube;

FIG. 7 is an illustration showing the construction of an inserted portion cover member;

FIG. 8 is an exploded view of the construction of a covered type endoscope;

FIG. 9 is an illustration showing a state of connection between an air supply tube, a water supply tube, an aspiration tube and the inserted portion cover member;

FIG. 10 is an illustration showing an example of a modification of the operated portion cover member;

FIGS. 12 to 15 relate to a fourth embodiment of the present invention;

FIG. 12 is an illustration showing the overall construction of a covered type endoscopic apparatus having a covered type endoscope;

FIG. 13 is an exploded view of the construction of the covered type endoscope;

FIG. 14 is a cross-sectional view of the construction of an operated portion cover member;

FIGS. 6 to 20 relate to a fifth embodiment of the present invention;

FIG. 16 is an illustration showing the overall construction of a covered type endoscopic apparatus having a covered type endoscope;

FIG. 17 is an illustration of the construction of an inserted portion cover member;

FIG. 18 is a cross-sectional view taken along the line 18—18 of FIG. 17;

FIGS. 19(a) and 19(b) are cross-sectional views of the inserted portion cover member in a diametral direction thereof;

FIG. 20 is an illustration of a state of connection of aspiration tubes at a three-way cock;

FIG. 21 is a cross-sectional view an operated endoscope portion fixation mouth member with respect to an aspiration passage alone;

FIG. 22 is an illustration of the construction of an inserted portion cover member.

DESCRIPTION OF THE PREFERRED EMBODIMENTS

Figure 1:
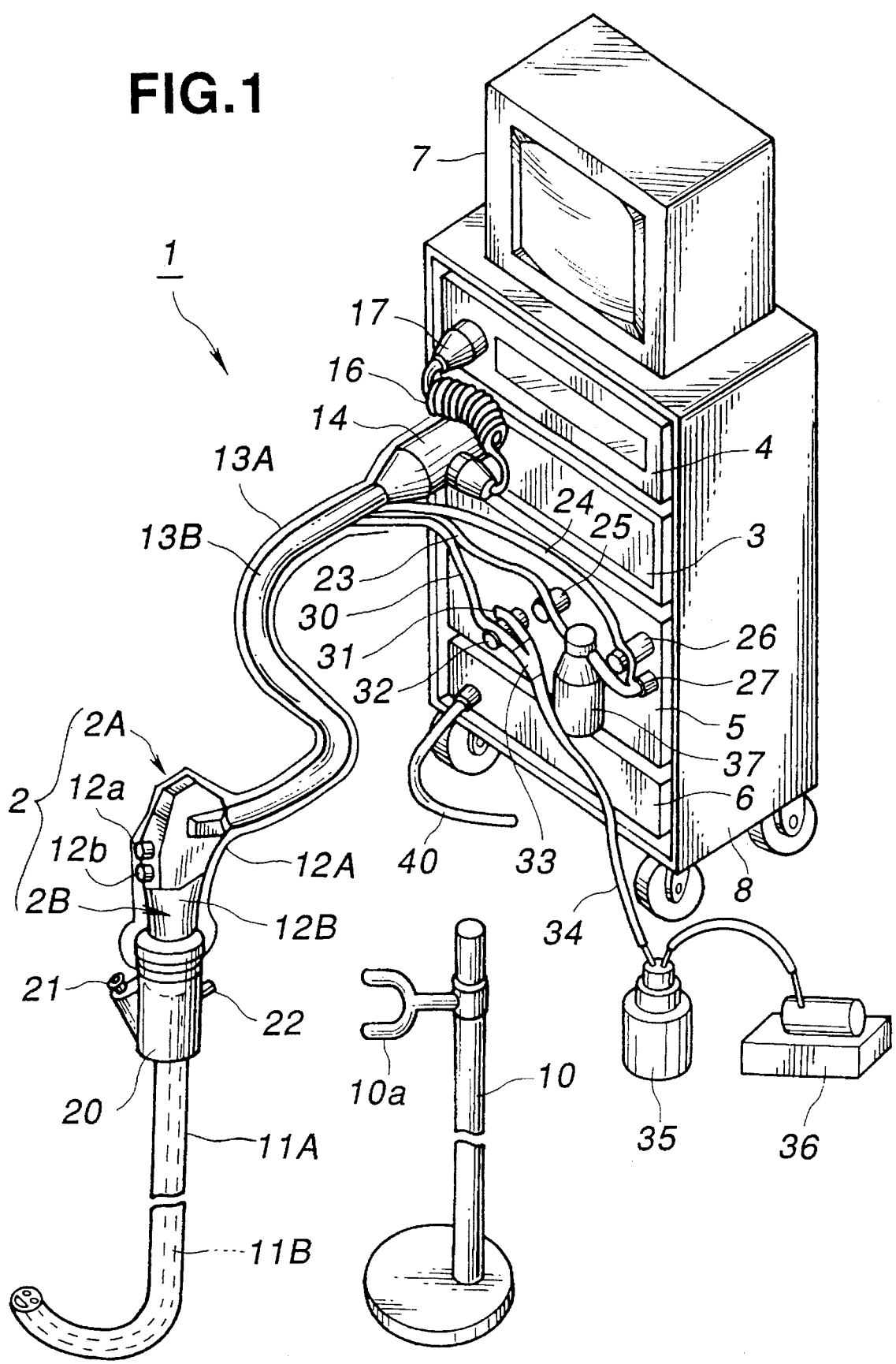

Referring to FIG. 1, a covered endoscope type of endoscopic apparatus (hereinafter referred to as "covered type endoscopic apparatus) 1 in accordance with a first embodiment of the present invention is composed of a covered type endoscope 2 formed of a channeled endoscope cover (hereinafter referred to simply as "cover") 2A and a covered endoscope 2B, a light source unit 3 for supplying illumination light to the covered endoscope 2B, a video processor 4 for processing a signal from an image pickup means incorporated in the covered endoscope 2B, a fluid control unit 5 for supplying air and water through tubes in the cover 2A, a channeled cover expander (hereinafter referred to simply as "cover expander") 6 used to set the covered endoscope 2B in the cover 2A, and a monitor 7 for displaying an image of an image signal processed by the video processor 4. The light source unit 3, the video processor 4, the fluid control unit 5 and the expander 6 are accommodated in a cart 8, and the monitor 7 is placed on an upper surface of the cart 8.

The covered type endoscope is characterized in that when an endoscopic examination is performed, the covered endoscope 2B maintained in a clean state is covered with a clean cover 2A. After the examination, the cover 2A is removed and discarded as waste, and the covered endoscope 2B is covered with a new clean cover 2A to be used repeatedly.

The covered endoscope 2B is formed of an inserted endoscope portion (hereinafter referred to simply as "inserted portion") 11B having an elongated shape and flexible, and an operated endoscope portion (hereinafter referred to simply as "operated portion") 12B formed at an base end of the inserted portion 11B, and a universal cord 13B extending from a side portion of the operated portion. A connector 14 provided on an extreme end of the universal cord 13B can be detachably connected to the light source unit 3. When the connector 14 is connected to the light source unit 13, illumination light from a lamp in the light source unit 13 can be supplied to an extreme end of a light guide (not shown) inserted through the universal cord 13B. A cable 16 is extending from the connector 14, and a signal connector 17 provided at an extreme end of the cable 16 is detachably connected to the video processor 4. An image signal outputted from an image pickup device (not shown) provided in the vicinity of a fore end of the inserted portion 11B is supplied through the cable 16 to be processed by the video processor 4, and a corresponding image can be observed through the monitor 7.

A bending operation knob (not shown) is provided on a side surface of the operated portion 12B opposite to the side from which a base end portion of the universal cord 13B extends. The bending operation knob serves to bend a bending portion of the inserted portion 11B provided on the fore end side. Also, the operated portion 12B is provided with air/water supply switch 12a, an aspiration switch 12b, and an image changeover switch (not shown) or the like. Each of operations for air supply, water supply, aspiration, and image freeze or the like can be performed by operating the corresponding switch.

The cover 2A is constituted of an inserted portion cover member 11A, an operated portion cover member 12A and a universal cord cover member (hereinafter referred to as "cord cover") 13A which cover the inserted portion 11B having a semicircular cross section, the operated portion 12B and the universal cord 13B of the covered endoscope 2B, respectively. An operated endoscope portion fixation mouth member 20 having a forceps inlet 21 and an expansion tube mouth 22, to which an expansion tube 40 provided on the expander is connected, is provided on a base end of the inserted portion cover member 11A.

A tubular air supply passage or air supply tube 24, a water supply tube 23 and an aspiration tube 30 inserted through the inserted portion cover member 11A, the operated portion cover member 12A and the cord cover 13A are connected to the fluid control unit 5. Intermediate portions of the air supply tube 24 and the water supply tube 23 are inserted in pinch valves 26 and 25, respectively, and these tubes are connected to an air supply port member 27 which communicates with an air supply pump (not shown) of the fluid control unit 5 through a water supply tank 37. The pinch valves 26 and 25 are controlled by the fluid control unit 5 in response to the operation of the air/water supply switch 12a so as to open the air supply tube 24 at the time of air supply and open the water supply tube 23 at the time of water supply.

An intermediate portion of the aspiration tube 30 is inserted in a pinch valve 32, and a branching member 33 is provided at an end of the aspiration tube 30, whereby the aspiration tube 30 diverges into aspiration tubes 31 and 34. An end of the aspiration tube 34 is connected to an aspiration pot 35 which is connected to an aspiration pump 36. The pinch valve 32 is controlled by the fluid control unit 5 in response to the operation of the aspiration switch 12b so as to open the aspiration tube 30 while closing the aspiration tube 31 at the time of an aspiration operation and so as to open the aspiration tube 31 while closing the aspiration tube 30 at the time of non-aspiration.

A cover supporting instrument 10 is provided to support the inserted portion cover member 11A when the inserted portion cover member 11A is fitted around the covered endoscope 2B. The inserted portion cover member 11A is supported by a semicircular supporting portion 10a of the cover supporting instrument 10 when fitted around the covered endoscope 2B.

Figure 2A:
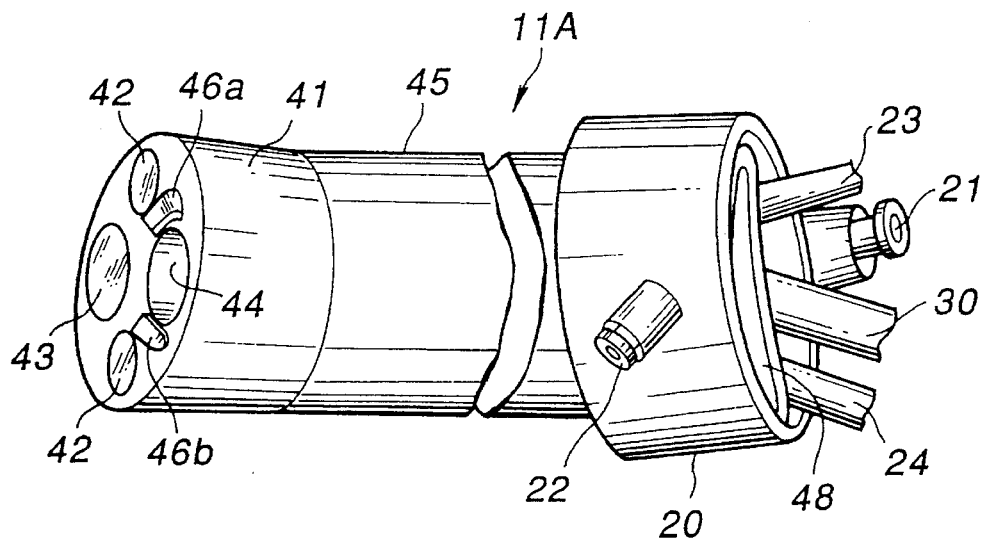
FIGS. 2(a) and 2(b) are illustrations showing the construction of an inserted portion cover member.
Figure 2B:
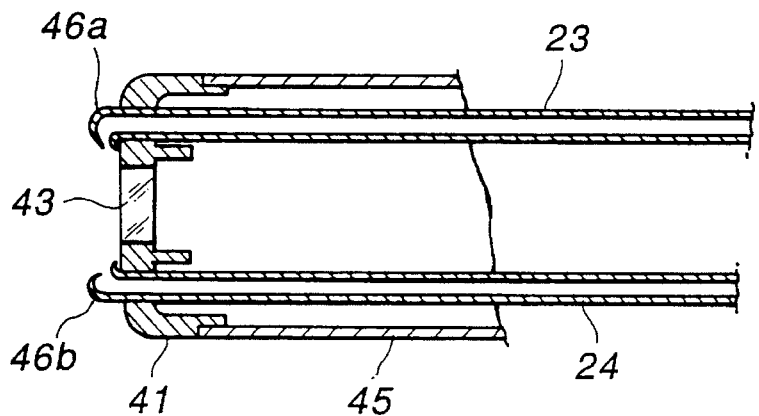

As shown in FIG. 2(a), the inserted portion cover member 11A has a fore end component portion 41 at its extreme end. The fore end component portion 41 has transparent windows 42 and 43 formed at positions corresponding to portions of an illumination optical system and an observation optical system provided at the fore end of the inserted portion 11B of the covered endoscope 2B. An inserted portion outer covering 45 for separating the inserted portion 11B of the covered endoscope 2B from the outside environment is connected to the fore end component portion 41 in an airtight manner. The above-mentioned operated endoscope portion fixation mouth member 20 is provided at the end of the inserted portion outer covering 45 on the operator side. As shown in FIG. 2(b), air supply and water supply nozzles 46a and 46b are formed integrally with the air supply tube 24 and the water supply tube 23 so as to have orifices facing the window 43.

An opening of an endoscope insertion channel 48 for insertion of the covered endoscope is formed at the end of the operated endoscope portion fixation mouth member 20 on the operator side. Also, the aspiration tube 30 having a mouth portion 44 formed in the fore end surface of the fore end component portion 41 and the air-supply tube 24 and water supply tube 23 connected to the air supply and water supply nozzles 46a and 46b extend out of the mouth member 20 on this side.

Figure 3:
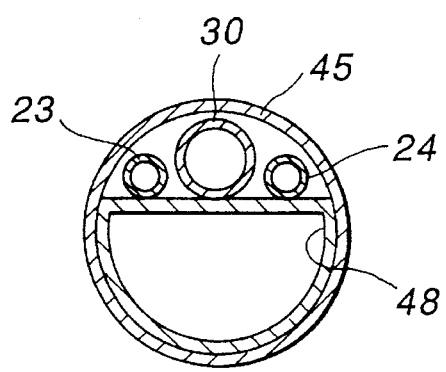

As shown in FIG. 3, the air supply tube 24 and the water supply tube 23 having a smaller outside diameter are disposed on the opposite sides of the aspiration tube 30 having a larger outside diameter. This layout enables the inserted portion cover member 11A to be reduced in diameter in comparison with a layout in which the air supply tube 24 and the water supply tube 23 are disposed on the same side of the aspiration tube 30. Also, the inserted portion cover member 11A in accordance with the layout of this embodiment has an approximately symmetric cross sectional configuration such that the force required to bend the bending portion is generally the same with respect to opposite bending directions and can be limited to a comparatively small value.

The parts for the connection between the fluid control unit 5 and the aspiration tube 30, the air supply tube 24 and the water supply tube 23 varying with respect to types of the covered endoscope 2B and incorporated in the inserted portion cover member may be used in common to facilitate the connection to the fluid control unit 5. Also, if the entire lengths of the tubes are provided as common parts, the cost of use can be reduced and a low-priced disposable product can be provided.

Figure 4:
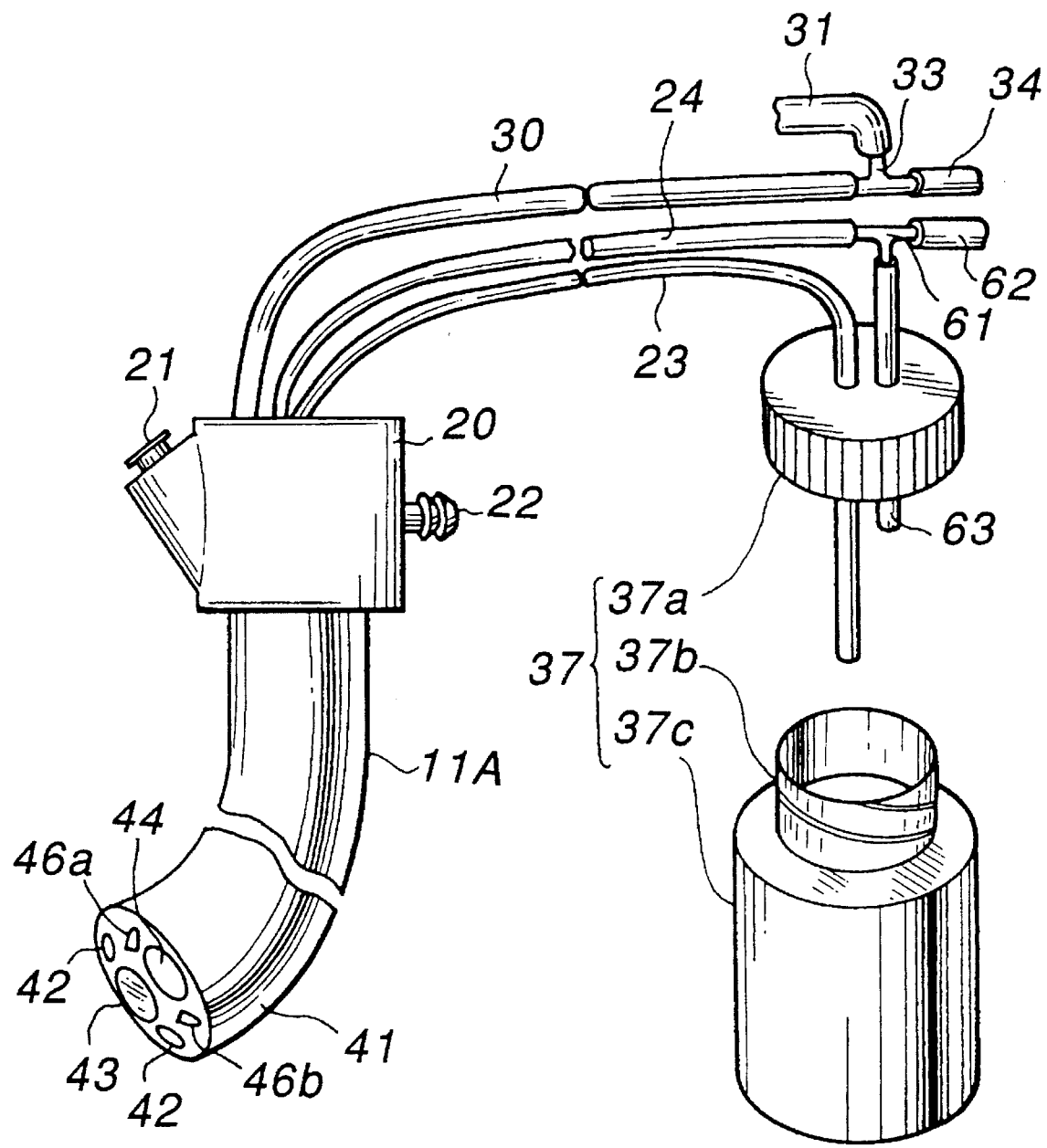

A cap 37a of the water supply tank 37 is formed integrally with portions of the air supply tube 24 and the water supply tube 23 from the inserted portion cover member 11A in the vicinity of ends of these tubes, as shown in FIG. 4. The air supply tube 24 diverges into an air supply tube 62 and an air supply tube 63 by a branching member 61. The air supply tube 63 and the water supply tube 23 are opened after passing through the cap 37a. The length of the water supply pipe 23 passing through the cap 37a is longer than the length of the corresponding portion of the air supply tube 63. The cap 37a is screwed around a threaded portion 37b of a main body 37c of the water supply tank 37. Tube portions in the vicinity of the water supply tank 37 are provided entirely integrally with the inserted portion cover member 11A. Thus, the entire tubes can be used as disposable parts. No tubes are included in the portion of the water supply tank 37 used repeatedly, and the water supply tank 37 can be easily washed and sterilized. Thus, the prevention of infection is facilitated.

Figure 5A:
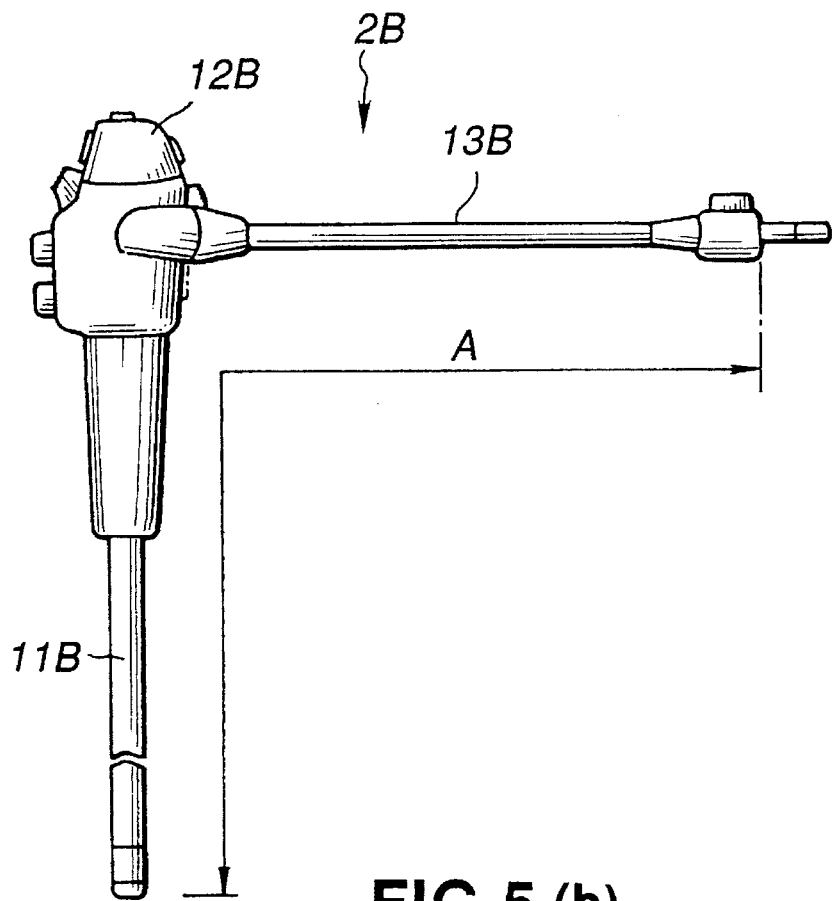
FIGS. 5(a) and 5(b) are illustrations showing the relationship between the overall length of the covered endoscope and the overall length of the cover including the air supply tube, the water supply tube and an aspiration tube.
Figure 5B:
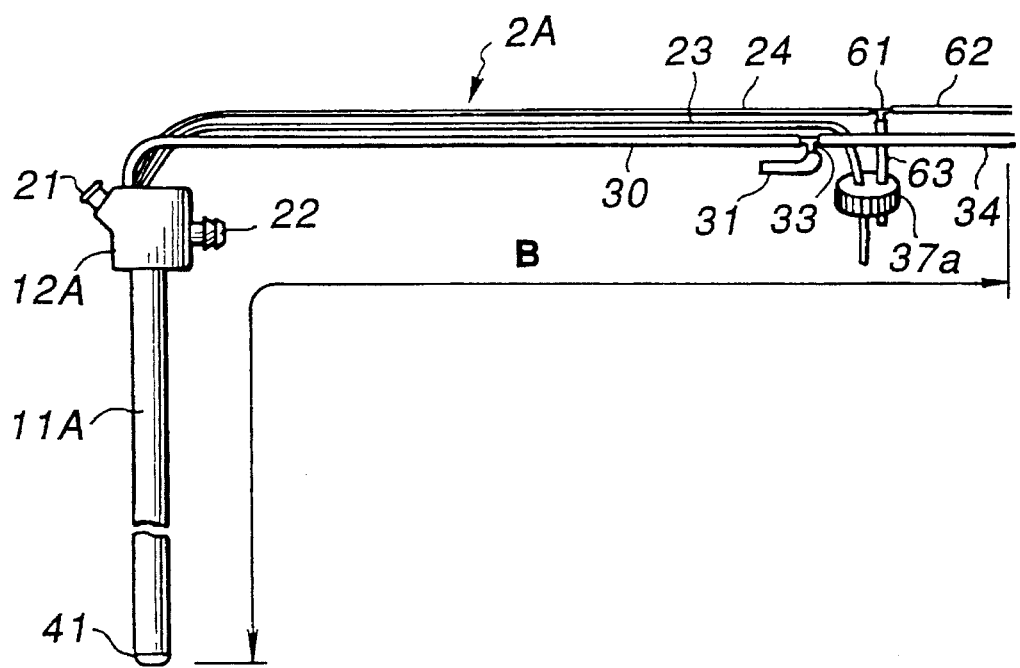

As shown in FIGS. 5(a) and 5(b), the overall length B (FIG. 5(b)) of each of the aspiration tube 30, the air supply tube 24 and the water supply tube 23 is selected as to be longer than the sum A (FIG. 5(a)) of the lengths of the inserted portion 11B and operated portion 12B of the covered endoscope 2B and the universal cord 13B.

The operation of the thus-constructed covered type endoscope will be described below.

The inserted portion cover member 11A of a sterilized endoscope cover 2A constructed as described above is taken out of an unillustrated cover storage package in which the endoscope cover 2A is packed, as in the case of the conventional ordinary endoscope cover setting method.

The cover expander 6 is used when the inserted portion 11B of the covered endoscope 2B is fitted in the inserted portion cover member 11A, or when the inserted portion 11B is removed from the inserted portion cover member 11A.

Basically, the cover expander 6 consists of an air supply pump and an air supply tube (not shown), and a mouthpiece to which the base end portion of the expansion tube 40 is connected is provided at an opening end of the air supply tube. The cover expander 6 normally continues supplying air. Therefore, when the function of the cover expander 6 is not used, the extreme end of the expansion tube 40 is not connected to the expansion tube mouth 22 and is open to the outside air so that air therein leaks out, as shown in FIG. 1.

When the covered endoscope 2B is inserted into or drawn out of the inserted portion cover member 11A, the extreme end of the expansion tube 40 is forced into the expansion tube mouth 22 while the upper-end flange portion of the operated endoscope portion fixation mouth member 20 is supported on the semicircular supporting portion 10a provided on the cover supporting instrument 10. The expansion tube is thereby inserted (fitted) into the mouth in an airtight manner. Then, air can be supplied into the endoscope insertion channel 48 via the expansion tube mouth 22 to expand the endoscope insertion channel 48, thereby enabling the inserted endoscope portion 11B to be easily inserted or drawn out.

Figure 6:
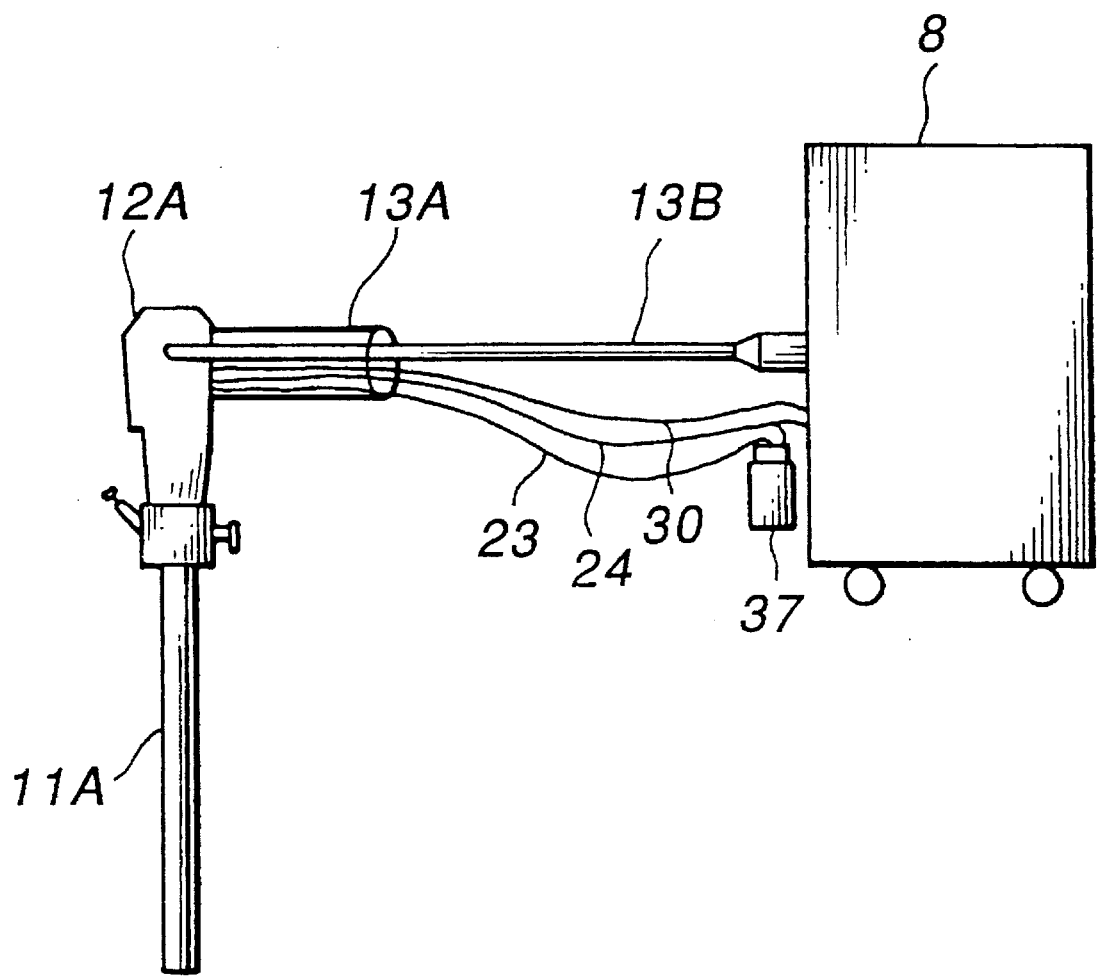

In the covered type endoscopic apparatus 1 in accordance with this embodiment, since the overall length B of the aspiration tube 30, the air supply tube 24 and the water supply tube 23 of the cover 2A is set so as to be longer than the sum of the lengths of the inserted portion 11B and the operated portion 12B of the covered endoscope 2B and the universal cord 13B, the aspiration tube 30, the air supply tube 24 and the water supply tube 23 are in a slack state, as shown in FIG. 6, when used for examination, even if the universal cord 13B is placed under tension. Therefore, even if the covered type endoscope 1 is pulled in a direction such as to move away from the cart 8, substantially no stress is caused in the aspiration tube 30, the air supply tube 24 and the water supply tube 23. Consequently, there is no risk of the aspiration tube 30, the air supply tube 24 or the water supply tube 23 coming off the fluid control unit 5, and it is possible to prevent any contamination of the examination room.

In this embodiment, the length of each of the aspiration tube 30, the air supply tube 24 and the water supply tube 23, exclusive of the air supply tube 62 and so on (length to the extreme end) may set so as to be longer than the overall length of the inserted portion 11B and the operated portion 12B of the covered endoscope 2B and the universal cord 13B, whereby the effect of this embodiment can be further improved.

If the inserted portion outer covering 45, the cap 37a and the air supply tube 63 are packed in the same sterilized package, they are easier to handle. If the branching member 61 and the air supply tube 62 are also packed together, the ease of handling is further increased. If the branching member 33 and the aspiration tubes 31 and 34 are also packed together, the handling performance can be further improved. Also, the inserted portion outer covering 45, the aspiration tube 30, the air supply tube 24, the water supply tube 23, the cap 37a, the air supply tube 63, the branching member 61, the air supply tube 62, the branching member 33, the aspiration tube 31 and the aspiration tube 34 may be packed in a plurality of sterilized packages.

A second embodiment of the present invention will be described below. The second embodiment is generally the same as the first embodiment. Therefore only different components or different points of the construction will be described and the same components are indicated by the same reference characters.

Figure 7:
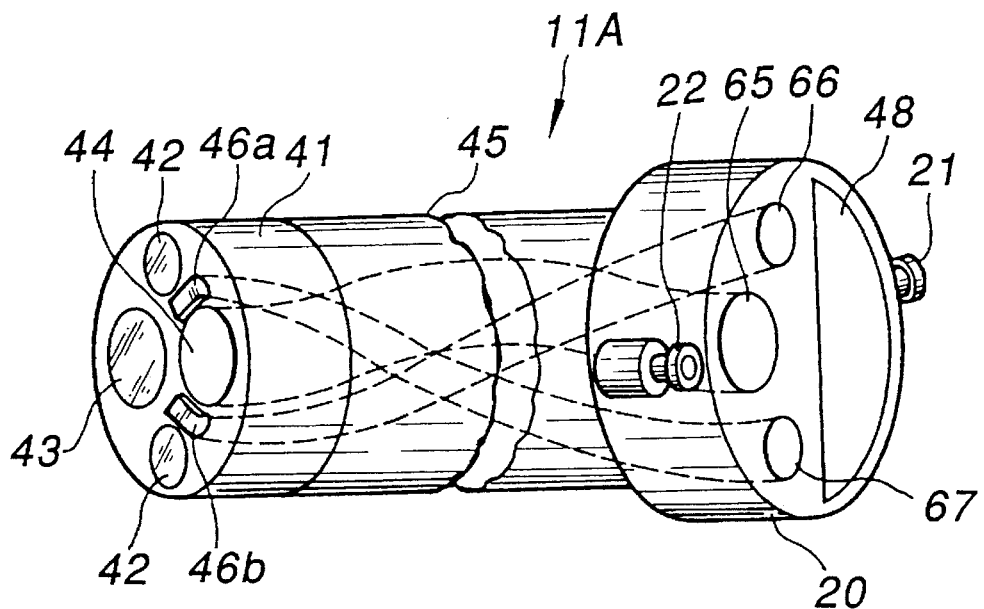
FIGS. 7 to 10 relate to a second embodiment of the present invention.

Referring to FIG. 7, air supply and water supply nozzles 46a and 46b are formed in an fore end surface of a fore end component portion 41 of an inserted portion cover member 11A for a covered type endoscope 2B. The nozzles 46a and 46b have orifices facing the above-mentioned window 43 and are formed integrally with a first air supply tube 67 and a first water supply tube 66 to which an air supply tube 24 and a water supply tube 23 are connected. A first aspiration tube 65 is provided adjacent to the first air supply tube 67 and the first water supply tube 66. The above-mentioned aspiration tube 30 having a mouth portion 44 formed in the fore end surface of the fore end component portion 41 is connected to the first aspiration tube 65. An opening of an endoscope insertion channel 48 for insertion of the covered endoscope is formed in an operated endoscope portion fixation mouth member 20 on the operator side thereof. The first air supply tube 67, the first water supply tube 66 and the first aspiration tube 65 extend while being twisted through 180° in the inserted portion outer covering 45 to communicate with the air supply and water supply nozzles 46a and 46b and the mouth portion respectively.

Figure 9:
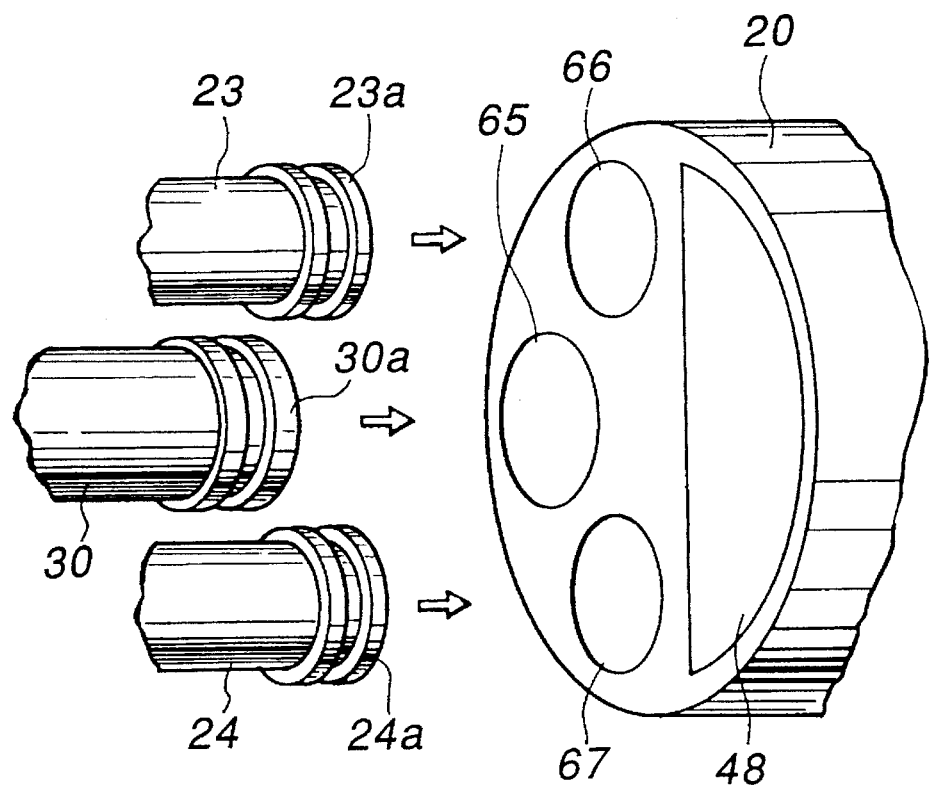
Figure 8:
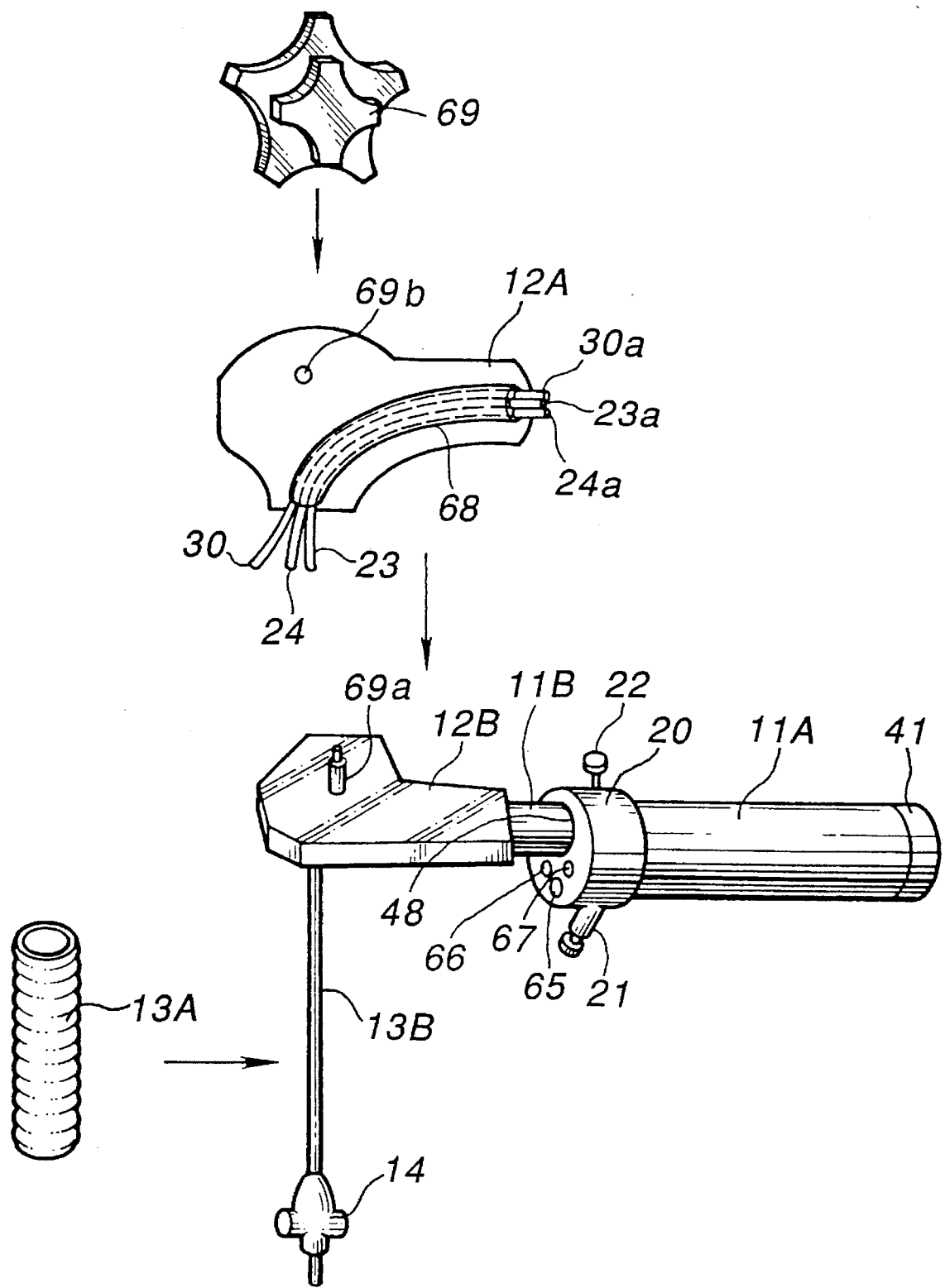

As shown in FIG. 8, an inserted portion 11B of the above-described covered type endoscope 2B is inserted into the endoscope insertion channel 48 of the inserted portion cover member 11A. When an operated portion cover 12A having a tube channel 68 through which the air supply tube 24, the water supply tube 23 and the aspiration tube 30 extend is attached, mouths 24a, 32a, and 30a provided on ends of the air supply tube 24, the water supply tube 23 and the aspiration tube 30 are connected to mouth portions of the first air supply tube 67, the first water supply tube 66 and the first aspiration tube 65, respectively (see FIG. 9). Thereafter, a bending shaft 69a extending from the operated portion 12B is passed through a bending shaft hole 69b formed in the operated portion cover 12A, and the operated portion cover 12A is then fitted on the operated portion 12B. A bending knob 69 is attached to the bending shaft 69a, and a cord cover 13A is set to cover a universal cord 13B. The bending shaft 69a is previously connected to a bending mechanism (not shown) in the operated portion 11B.

Except for these points, the construction and the function of the second embodiment are the same as those of the first embodiment.

In the covered type endoscopic apparatus in accordance with the second embodiment, as described above, the first air supply tube 67, the first water supply tube 66, the first aspiration tube 65, the air supply tube 24, the water supply tube 23 and the aspiration tube 30 are detachably arranged, and it is therefore possible to fit the covered endoscope 2B in the endoscope insertion channel 48 of the inserted portion cover member 11A while these tubes are detached. Fitting operations can therefore be performed easily without contaminating the inserted portion cover member 11A. Also, since the air supply tube 24, the water supply tube 23 and the aspiration tube 30 are inserted through the tube channel 68 of the operated portion cover member 12A, the tubes are prevented from separating from each other during examination and the operability during operation can be improved.

Figure 10:
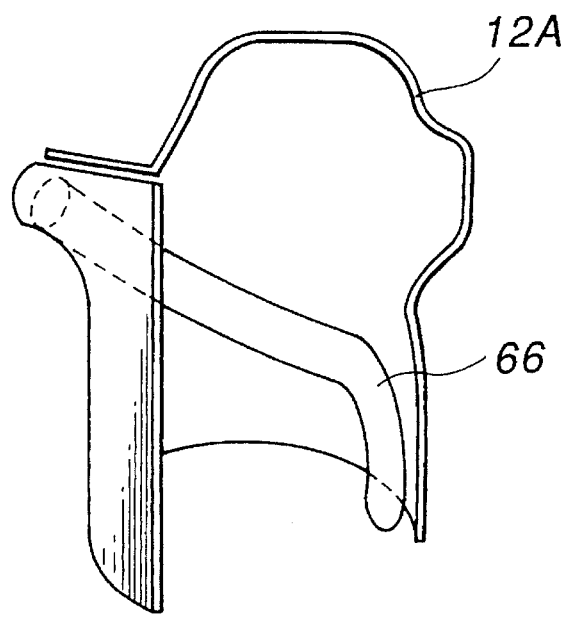

The tube channel 68 provided on the operated portion cover member 12A may be formed so as to project inside the operated portion cover member 12A, as shown in FIG. 10. It is possible to form a smooth outside surface of the operated portion cover member 12A such that the operator can grip the operated portion cover member 12A without an uneasy feeling.

The aspiration tube 30, the air supply tube 24 and the water supply tube 23 may be formed of a multi-lumen tube, and the air supply tube and the water supply tube may be provided integrally with each other, or the air supply tube, the water supply tube and the aspiration tube may be provided integrally, thereby facilitating handling of the tubes during examination. Also, the aspiration tube 30, the air supply tube 24 and the water supply tube 23 may be integrally bound with a band, a hook or the like.

A third embodiment of the present invention will be described below. The third embodiment is generally the same as the second embodiment except that the construction of a cord cover is different. Therefore only different components or different points of the construction will be described and the same components are indicated by the same reference characters.

Figure 11:
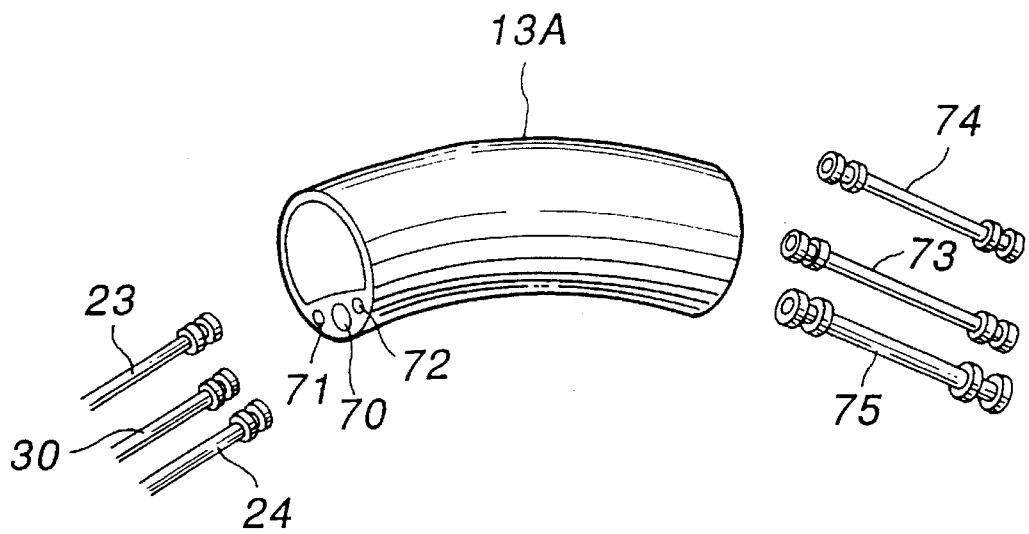
FIG. 11 is a perspective view of a cord cover in accordance with a third embodiment of the present invention.

Referring to FIG. 11, a second air supply tube 72, a second water supply tube 71 and a second aspiration tube 70 are provided in a cord cover 13A of the third embodiment. A third air supply tube 73, a third water supply tube 74 and a third aspiration tube 75 inserted through an operated portion cover member 12A and communicating with a first air supply tube 67, a first water supply tube 66 and a first aspiration tube 65 of an inserted portion cover member 11A are detachably connected to mouth portions of the second air supply tube 72, the second water supply tube 71 and the second aspiration tube 70 at an end of the cord cover 13A on the operator side. An air supply tube 24, a water supply tube 23 and an aspiration tube 30 are detachably connected to mouth portions of the second air supply tube 72, the second water supply tube 71 and the second aspiration tube 70 at the opposite end of the cord cover 13A. Except for these points, the construction and function of this embodiment are the same as those of the first embodiment.

In accordance with third embodiment described above, the air supply line, the water supply line and the aspiration line are also sectioned at the cord cover 13A to enable the cord cover 13A to be easily attached, while the same effects as those of the first embodiment are achieved.

A fourth embodiment will be described below. The fourth embodiment is generally the same as the second embodiment except that the construction of tubes for air supply, water supply and aspiration, the construction of an operated portion cover member, and the arrangement of switches for air supply, water supply, aspiration, image changeover and other operations are different from those of the second embodiment. Therefore, only different components or different points of the construction will be described and the same components are indicated by the same reference characters.

Figure 12:
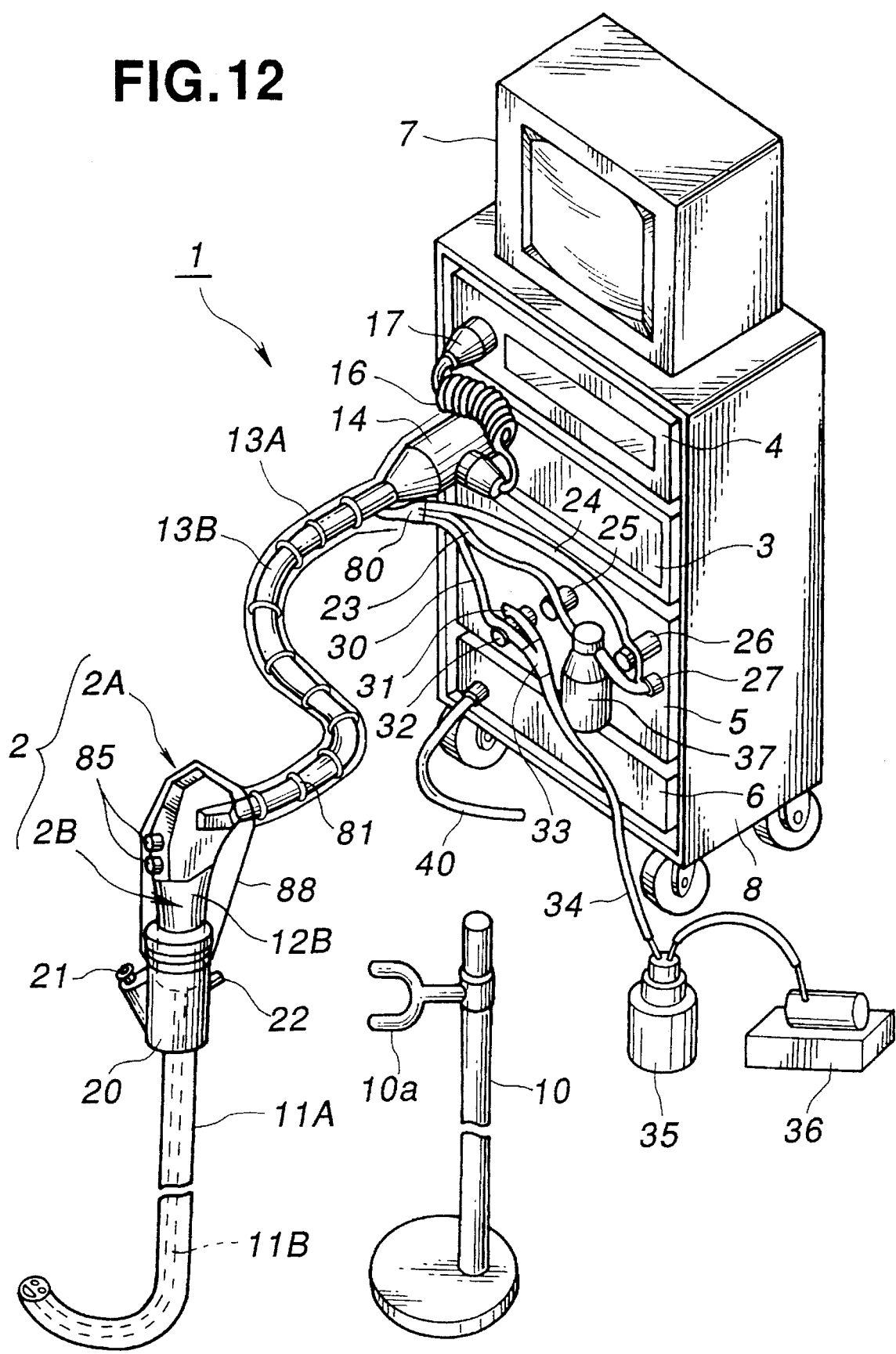

Referring to FIG. 12, an operated portion cover member 88 is formed of a hard plastic such as polyethylene, and a multi-lumen tube 81 incorporating an air supply tube B, a water supply tube B and an aspiration tube B described later and spirally formed is spirally wound around a universal cord 13B.

Figure 13:
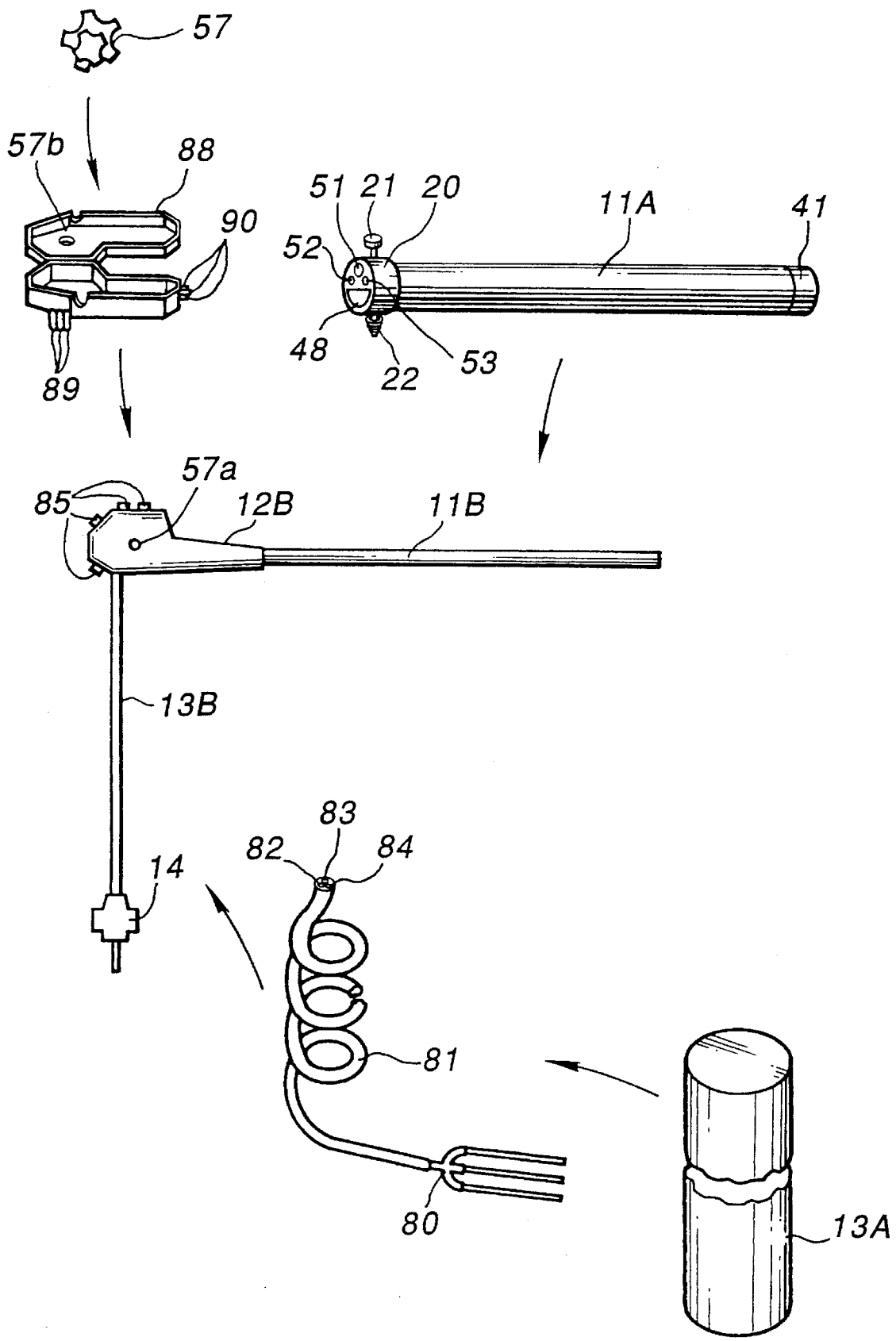
Figure 14:
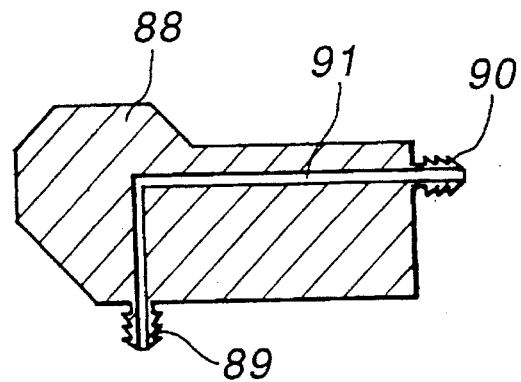

FIG. 13 shows a state of a cover 2A before the cover 2 is fitted around a covered endoscope 2B. The operated portion cover member 88 is formed so as to have a cavity for accommodating an operated portion 12B. An air supply tube 91 having at its opposite ends mouth members 89 and 90 as shown in FIG. 14, a water supply tube A (not shown) and an aspiration tube A (not shown) are also incorporated in the operated portion cover member 88. Mouth members 89 of the air supply tube A, the water supply tube A and the aspiration tube A are disposed so as to be able to connect to mouth portions of a tubular air supply passage B82, a tubular water supply passage B84 and a tubular aspiration passage B83 in the multi-lumen tube 81. The tubular air supply passage B82, the tubular water supply passage B84 and the tubular aspiration passage B83 of the multi-lumen tube 81 are separated by a branching member 80 to be connected to an air supply tube 24, a water supply tube 23 and an aspiration tube 30 which are connected to a fluid control unit 5. The multi-lumen tube 81 is spirally wound around the universal cord 13B. On the other hand, mouth members 90 are disposed so as to be able to connect to mouth portions of a first air supply tube 53, a first water supply tube 52 and a first aspiration tube 51. A bending knob 57 is attached to a bending shaft 57a, and the universal cord 13B is covered with a cord cover 13A.

Figure 15A:
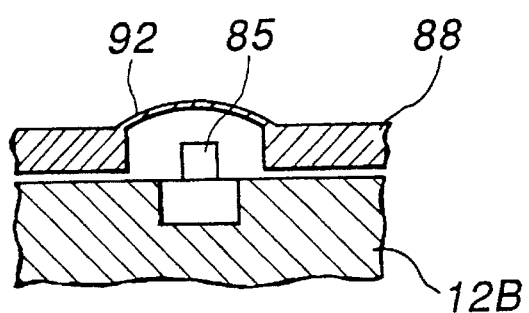
FIGS. 15(a) and 15(b) are cross-sectional views of the construction of an air/water supply switch, an aspiration switch and an image changeover switch.
Figure 15B:
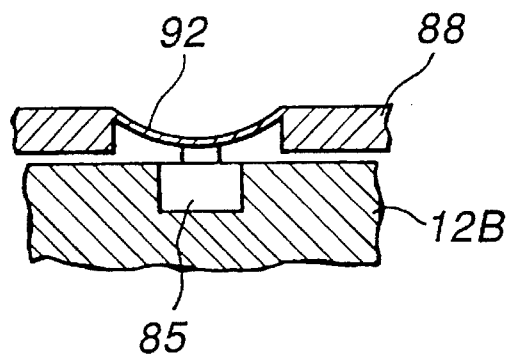

Switches 85 for air supply, water supply, aspiration, photography release and other operations are provided on the operated portion 12B. A thin diaphragm 92 is formed as a portion of the operated portion cover member 88 facing these switches 85, as shown in FIG. 15(a). The diaphragm 92 is pressed and deformed to press and operate each switch 85, as shown in FIG. 15(b). By using this structure, the operated portion cover member 88 can have a smooth shape such that the washability of the cover is improved.

A fifth embodiment of the present invention will be described below. The fifth embodiment is generally the same as the first embodiment. Therefore only different components or different points of the construction will be described and the same components are indicated by the same reference characters.

Figure 16:
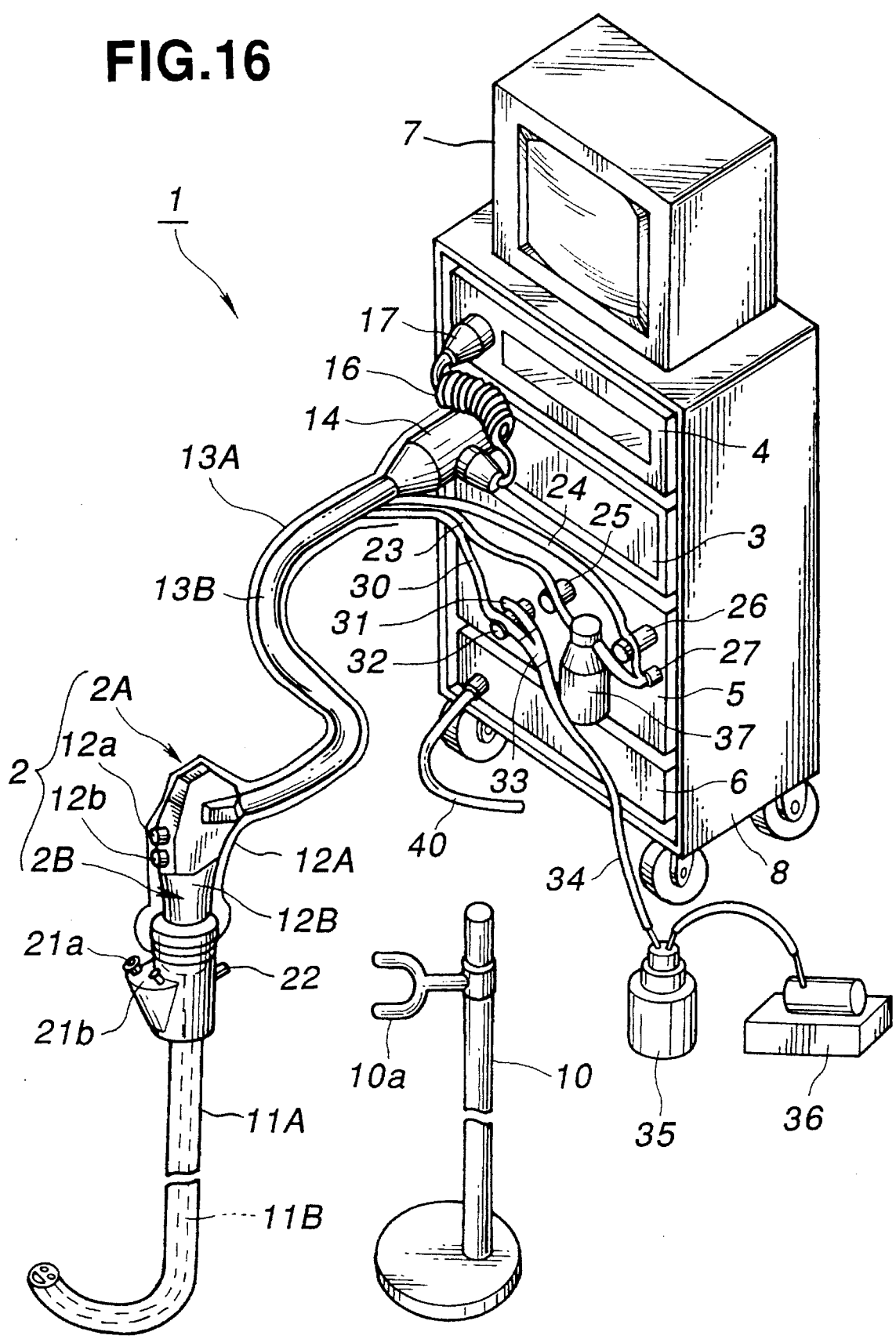

Referring to FIG. 16, an operated endoscope portion fixation mouth member 20 having treatment instrument inlets 21a and 21b and an expansion tube mouth 22 to which an expansion tube 40 provided on an expander 6 is connected is provided on a base end portion of an inserted portion cover member 11A. The expansion tube mouth 22 is provided opposite to the treatment instrument inlets 21a and 21 and it does not interfere with treatment instrument operations.

Figure 17:
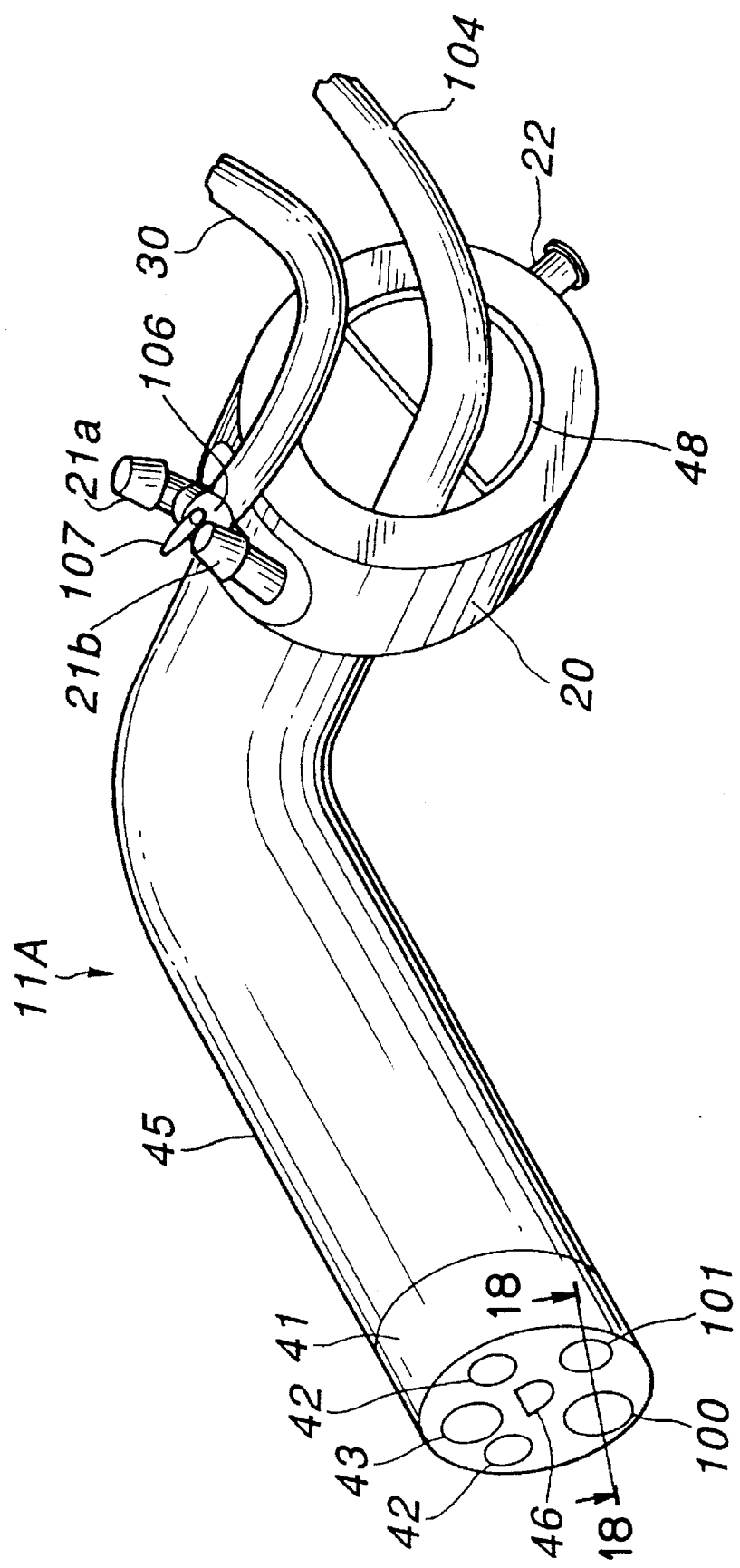

Referring then to FIG. 17, the inserted portion cover member 11A is constituted of a fore end component portion 41 which has transparent windows 42 and 43 formed at positions corresponding to portions of an illumination optical system and an observation optical system provided at a fore end of an inserted portion 11B of a covered endoscope 2B, and to which an inserted portion outer covering 45 for separating the inserted portion 11B of the covered endoscope 2B from the external environment is connected in an airtight manner. The operated endoscope portion fixation mouth member 20 is disposed at the end of the inserted portion outer covering 45 on the operator side. An air/water supply nozzle 46 having an orifice facing the window 43 is also provided in the fore end component portion 41. The air/water supply nozzle 46 is integrally formed in an air supply/water supply tube preferably 104 which is formed of a double lumen tube made of Polytetrafluoroethylene, and which is connected to an air supply tube 24 and a water supply tube 23.

A mouth portion of an endoscope insertion channel 48 for insertion of the covered endoscope is formed in the operated endoscope portion fixation mouth member 20 on the operator side, and the air supply/water supply tube 104 projects from the mouth member 20 on this side. A first aspiration tube 100 and a second aspiration tube 101 diverging from an aspiration tube 101 and having mouths opened in the fore end surface of the fore end component portion 41 extend through the inserted portion outer covering 45. The first aspiration tube 100 and the second aspiration tube 101 communicate with the treatment instrument inlets 21a and 21b.

Figure 18:
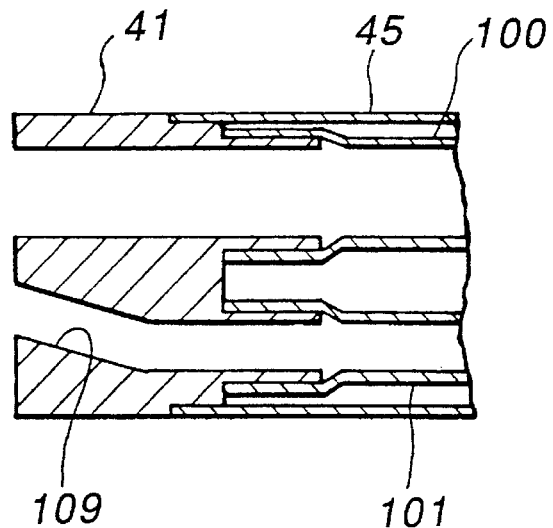

As shown in FIG. 18 which is a cross-sectional view taken along the line 18—18 of FIG. 17, an internal portion of the cover fore end component portion 41 forming a mouth portion extending from the end of the second aspiration tube 101 has a slanted portion 105 inclined toward the first aspiration tube 100. Therefore, a treatment instrument inserted through the treatment instrument inlet 21b and the second aspiration tube 101 projects toward a treatment instrument inserted through the treatment instrument inlet 21a and the first aspiration tube 100. A kind of operation, such as a strip biopsy operation, requiring associated use of a plurality of treatment instruments is facilitated by this arrangement.

Figure 19:
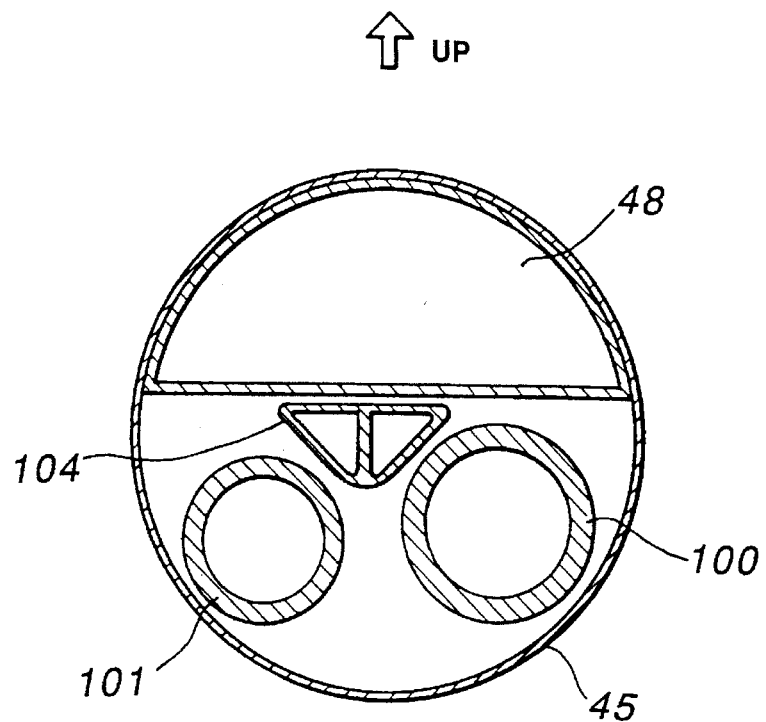
Figure 19:
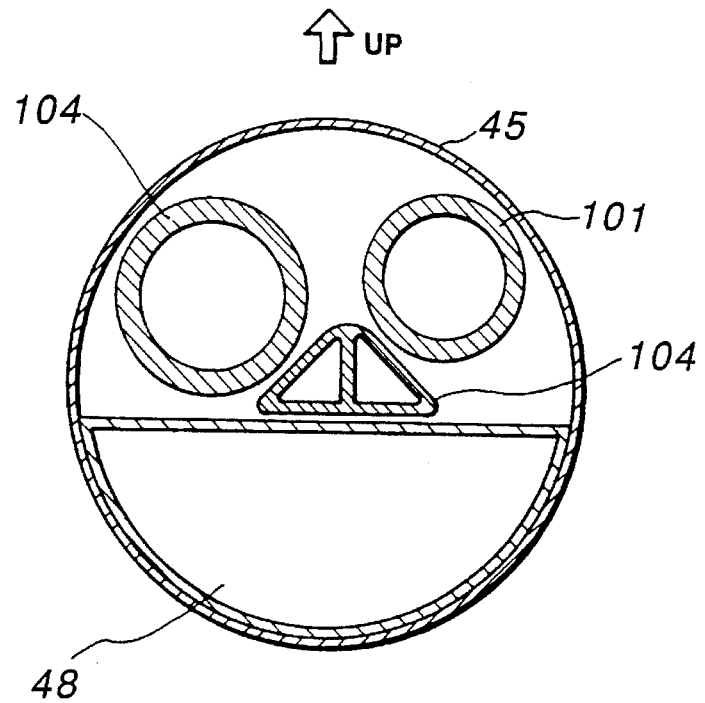

FIG. 19(a) shows a cross section of a portion of the covered endoscope close to the cover fore end component portion 41, and FIG. 19(b) shows a cross section of a portion close to the operated endoscope portion fixation mouth member 20. As illustrated, the first aspiration tube 100, the second aspiration tube, the air supply/water supply tube 104 positioned so as to be interposed between the first and second aspiration tubes 100 and 101, and the endoscope insertion channel 48 for insertion of the covered endoscope are incorporated. Since the air supply/water supply tube 104 is positioned between the first aspiration tube 100 and the second aspiration tube 101, the tubes can be laid efficiently and the outside diameter of the inserted portion can be reduced. The incorporated tubes are twisted through 180° from the cover fore end component portion 41 to the operated endoscope portion fixation mouth member 20 to realize a layout such that treatment instruments project at lower positions on the observed object side while the treatment inlets 21a and 21b formed in upper positions on the operated endoscope portion fixation mouth member 20.

Figure 20:
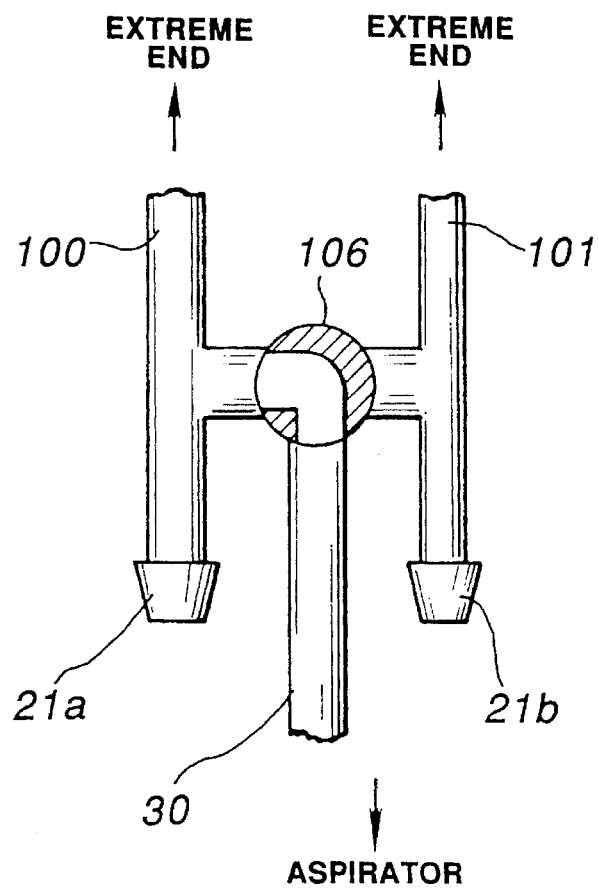

Next, a portion for communication between the first and second aspiration tubes 100 and 101, the first and second treatment instrument inlet 21a and 21b and the aspiration tube 30 will be described. As shown in FIG. 20, one of two tubes diverging from the first aspiration tube 100 communicates with the first treatment instrument inlet 21, and the other communicates with a port of a three-way cock 106. Also, one of two tubes diverging from the second aspiration tube 101 communicates with the second treatment instrument inlet 21b, and the other communicates with another port the three-way cock 106. A third port of the three way cock 106 communicates with the aspiration tube 30. A lever 107 (FIG. 17) is provided on the three-way cock 106. It is possible to select one of three communication modes: a mode of providing a communication between the first aspiration tube 100 and the aspiration tube 30, a mode of providing a communication between the second aspiration tube 101 and the aspiration tube 30, and a mode of simultaneously providing a communication between the first and second aspiration tubes 100 and 101 and the aspiration tube 30 by rotating the lever 107. Except for the above-described points, the construction and function of this embodiment are the same as those of the first embodiment.

In the covered type endoscopic apparatus of this embodiment, one of three modes of a communication between the first aspiration tube 100 and the aspiration tube 30, a communication between the second aspiration tube 101 and the aspiration tube 30, and a communication between the first and second aspiration tubes 100 and 101 and the aspiration tube 30 can be selected by rotating the lever 107 of the three-way cock 106, that is, an operator can easily select one of a plurality of modes of communication between the first aspiration tube 100, the second aspiration tube 101 and the aspiration tube 30. Thus, the operability with respect to aspiration operations is improved.

A sixth embodiment of the present invention will be described below. The sixth embodiment is generally the same as the fifth embodiment except that the aspiration tube connection structure is different from that of the fifth embodiment. Therefore only different components or different points of the construction will be described and the same components are indicated by the same reference characters.

Figure 21:
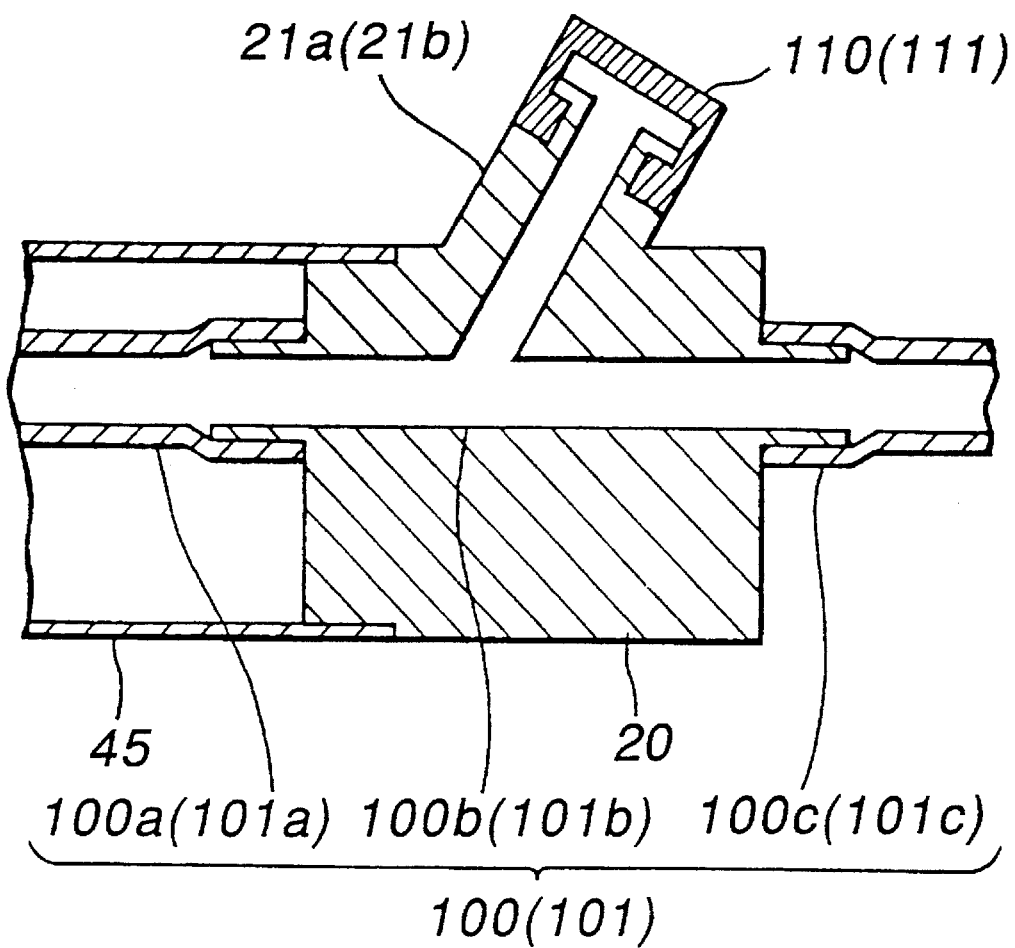
FIGS. 21 to 22 relate to a sixth embodiment of the present invention.

Referring to FIG. 21, a first tubular aspiration passage 100 (second tubular aspiration channel 101) is sectioned into a first tubular aspiration passage or aspiration tube (A) 100a (second tubular aspiration passage (A) 101a) in an inserted portion outer covering 45, a first tubular aspiration passage (B) 100b (second tubular aspiration passage 101b) in an operated endoscope portion fixation mouth member 20, and a first tubular aspiration passage or aspiration tube (C) 100c (second tubular aspiration passage (B) 101c) extending out of the operated endoscope portion fixation mouth member 20 on the operator side. The first tubular aspiration passage (B) 100b (second tubular aspiration passage (B) 101b) diverges inside the operated endoscope portion fixation mouth member 20 to communicate with a first treatment instrument inlet 21a (second treatment instrument inlet 21b). A first forceps stopper 110 (second forceps stopper 111) for presenting contamination is attached to an end of the first treatment instrument inlet 21a (second treatment instrument inlet 21b).

Figure 22:
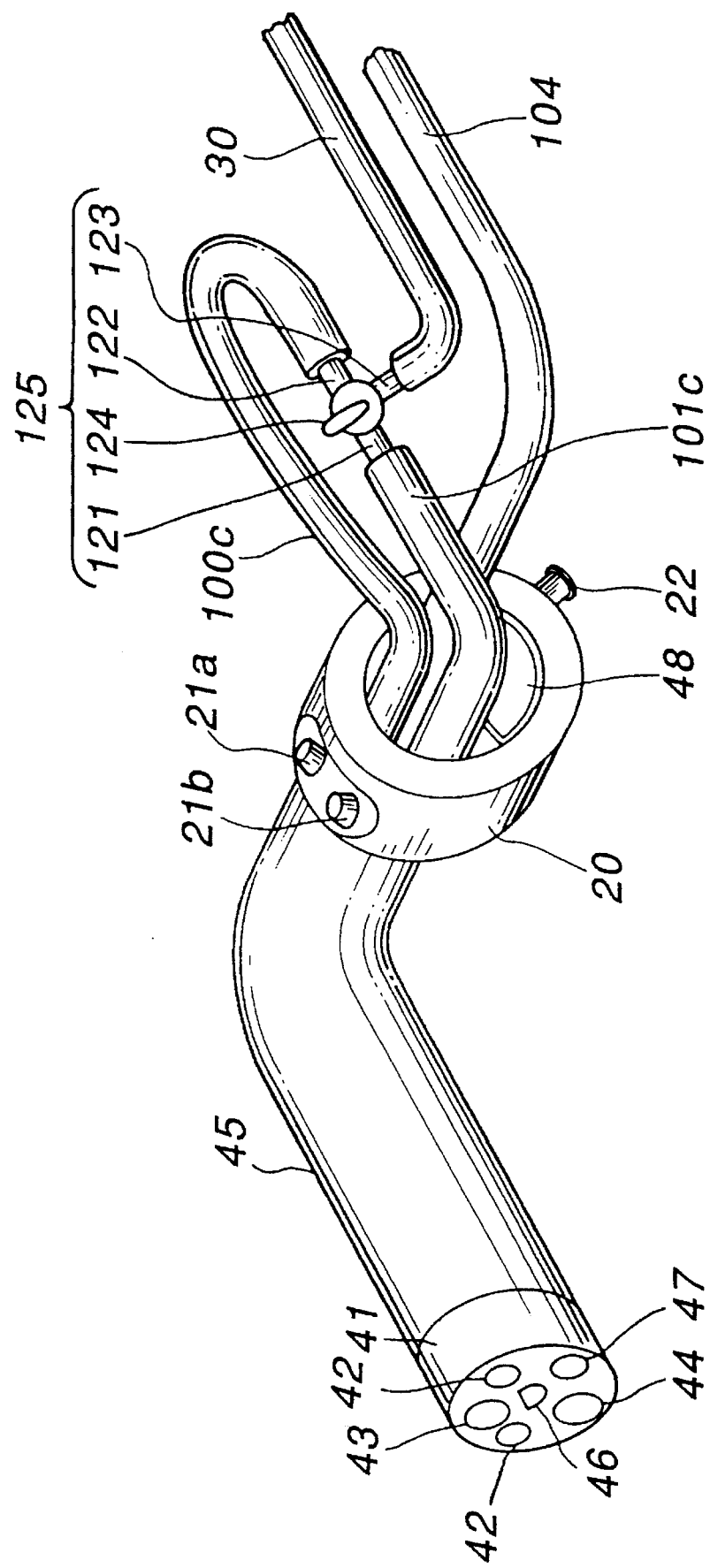

As shown in FIG. 22, the first aspiration tube (C) 100c and the second aspiration tube (C) 101a are connected to a first mouth 122 and a second mouth 121 of a three-way cock 125, respectively. A third mouth 123 of the three-way cock 125 communicates with an aspiration tube 30. It is possible to select one of three communication modes: a mode of providing a communication between the first aspiration tube (C) 100c and the aspiration tube 30, a mode of providing a communication between the second aspiration tube (C) 101c and the aspiration tube 30, and a mode of simultaneously providing communications between the first aspiration tube (C) 100c, the second aspiration tube (C) 101c and the aspiration tube 30. It is desirable to position the three-way cock 125 at a distance of 10 to 50 cm from an operated portion 12B of a covered endoscope 2B. Since the three-way cock exists in a universal cord cover 13B, the three-way cock 125 is changed by receiving an operating force through the cord cover 13B. Except for these points, the construction and function are the same as those of the fifth embodiment.

According to the sixth embodiment, as described above, the structure around the operated endoscope portion fixation mouth member 20 can be simplified to provide the apparatus at a reduced cost, while the advantages of the fifth embodiment are also achieved.

A seventh embodiment of the present invention will be described below. The seventh embodiment is generally the same as the sixth embodiment. Therefore only different components or different points of the construction will be described and the same components are indicated by the same reference characters.

The structure of a first aspiration tube (C) 100c and a second aspiration tube (C) 101c of the seventh embodiment is different from the corresponding structure of the sixth embodiment.

Figure 23:
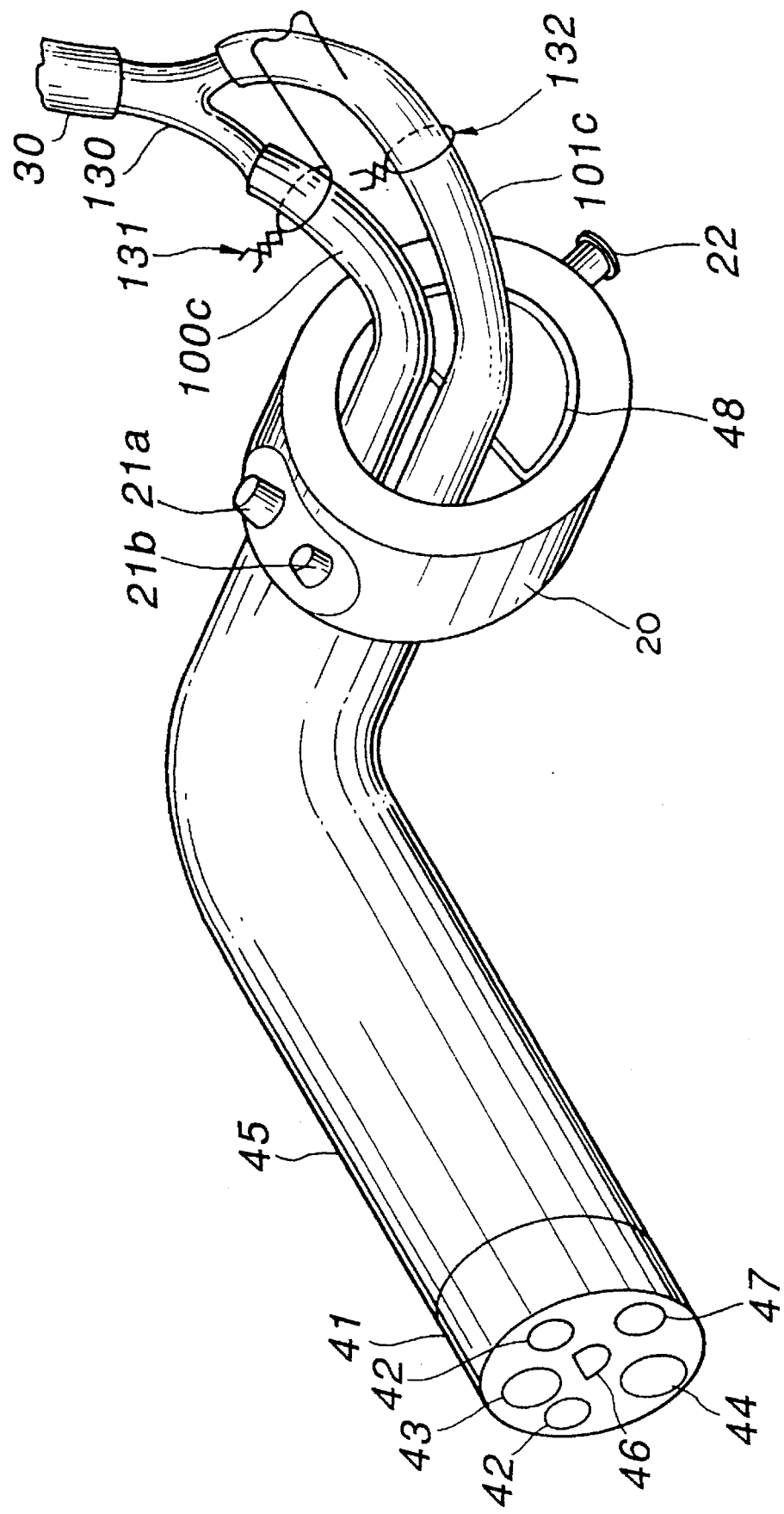
FIG. 23 is an illustration of the construction of an inserted portion cover member in accordance with a seventh embodiment of the present invention.

As shown in FIG. 23, the first aspiration tube (C) 100c and the second aspiration tube (C) 101c are connected by a three-way member 130, and pinch valves 131 and 132 are provided on intermediate portions of the first aspiration tube (C) 100c and the second aspiration tube (C) 101c. An operator opens or closes the pinch valves 131 and 132 according to need. Except for these points, the construction and function are the same as those of the sixth embodiment.

The embodiments have been described as covered endoscope type endoscopic apparatuses in which a direct-vision type endoscope is fitted in a cover. However, needless to say, the present invention can be applied to any other endoscopes, for example, a covered endoscope type endoscopic apparatus in which a side-vision type covered endoscope is fitted in a cover having transparent windows at positions corresponding to an illumination optical system and an observation optical system of the side-vision type covered endoscope.

Also, each of the covered endoscopes of the above-described embodiments is an electronic endoscope which images an observed image with an incorporated image pickup device, but this is not exclusively adopted. The present invention can also be applied to a covered type endoscopic apparatus using a covered endoscope which transmits an observed image through an optical image guide.

It is apparent that other widely different embodiments of this invention can be made without departing from the spirit and scope thereof, and it is to be understood that the invention is not limited to the specific embodiments thereof except as defined in the appended claims.

What is claimed is:

1. A covered endoscope type endoscopic apparatus comprising:

an endoscope having an inserted portion inserted into a body cavity to obtain an observed image, and transmission means for transmitting the observed image, said transmission means consisting of an operated portion formed at a base end of said inserted portion and a universal cord extending from a side portion of said operated portion;

an endoscope cover capable of being fitted around said endoscope and having a fore end component portion, a base end component portion and a soft tubular portion; and at least one fluid passage having at least a portion provided in said tubular portion;

wherein the overall length of said fluid passage is greater than the overall length of said endoscope including said inserted portion and said transmission means.

2. A covered endoscope type endoscopic apparatus according to claim 1, wherein said fluid passage has a mouth portion in said fore end component portion and serves to aspirate a fluid in the vicinity of said fore end component portion.

3. A covered endoscope type endoscopic apparatus according to claim 1 or 2, wherein said endoscope cover and said fluid passage are accommodated in one sterilized pack.

4. A covered endoscope type endoscopic apparatus comprising:

an endoscope having an inserted portion inserted into a body cavity to obtain an observed image, and transmission means for transmitting the observed image, said transmission means consisting of an operated portion formed at a base end of said inserted portion and a universal cord extending from a side portion of said operated portion;

an endoscope cover capable of being fitted around said endoscope and having a fore end component portion, a base end component portion and a soft tubular portion;

a liquid supply passage provided in said tubular portion to supply a liquid to a fore end of said endoscope cover;

a gas supply passage provided in said tubular portion to supply a gas to the fore end of said endoscope cover; and an aspiration passage provided in said tubular portion to aspirate the fluid from the fore end of said endoscope cover;

wherein said aspiration passage is placed between said liquid supply passage and said gas supply passage and wherein the overall length of any one of said passages is greater than the overall length of said endoscope including said inserted portion and said transmission means.

5. A covered endoscope type endoscopic apparatus comprising:

an endoscope having an inserted portion inserted into a body cavity to obtain an observed image, and transmission means for transmitting the observed image, said transmission means consisting of an operated portion formed at a base end of said inserted portion and a universal cord extending from a side portion of said operated portion;

an endoscope cover capable of being fitted around said endoscope and having a fore end component portion, a base end component portion and a soft tubular portion;

at least one fluid passage provided at least partially inside said tubular portion;

said endoscope cover including an operated portion cover for covering an operated portion of said endoscope; and positioning means for positioning said fluid passage on said operated portion cover and wherein the overall length of said at least one fluid passage is greater than the overall length of said endoscope including said inserted portion and said transmission means.

6. A covered endoscope type endoscopic apparatus according to claim 5, wherein said positioning means comprises a channel through which said fluid passage extends.

7. A covered endoscope type endoscopic apparatus comprising:

an endoscope having an inserted portion inserted into a body cavity to obtain an observed image, and transmission means for transmitting the observed image, said transmission means consisting of an operated portion formed at a base end of said inserted portion and a universal cord extending from a side portion of said operated portion;

an endoscope cover capable of being fitted around said endoscope and having a fore end component portion, a base end component portion and a soft tubular portion;

a plurality of fluid passages provided inside said tubular portion;

said plurality of fluid passages including at least a first fluid passage and a second fluid passage;

each of said first fluid passage and said second fluid passage having a mouth portion in said fore end component portion; and the mouth portion of one of said first and second fluid passages oriented toward a distal end surface of said fore end component portion and facing the mouth portion of the other of said first and second fluid passages.

* * * * *